United States Patent [19]

Crenshaw et al.

[11] 4,102,885
[45] Jul. 25, 1978

[54] PROCESS FOR PREPARING 2,4-DIHALOQUINAZOLINES

[75] Inventors: Ronnie Ray Crenshaw, Dewitt; George Michael Luke, Lafayette; Richard Anthony Partyka, Liverpool, all of N.Y.

[73] Assignee: Bristol-Myers Company, New York, N.Y.

[21] Appl. No.: 807,938

[22] Filed: Jun. 20, 1977

[51] Int. Cl.$^2$ ............................................ C07D 239/95
[52] U.S. Cl. ...................................... 544/283; 560/29; 560/32; 544/286; 544/285
[58] Field of Search ..................................... 260/251 Q

[56] References Cited

U.S. PATENT DOCUMENTS

| 3,511,836 | 5/1970 | Hess | 260/256.4 |
| 3,517,005 | 6/1970 | Cronin et al. | 260/256.4 |
| 3,769,286 | 10/1973 | Hess | 260/251 Q |
| 3,843,652 | 10/1974 | Findeisen et al. | 260/251 Q |

FOREIGN PATENT DOCUMENTS 2,261,739   6/1974   Fed. Rep. of Germany.

OTHER PUBLICATIONS

Curd et al., J. Chem. Soc., 1759 (1948).
Findeisen et al. (II), Synthesis, 599–605 (1972).
Budesinsky et al., Coll. Czech. Chem. Commun., 37, 2779 (1972).

Primary Examiner—Raymond V. Rush
Attorney, Agent, or Firm—Robert H. Uloth

[57] ABSTRACT

A one-step process for the preparation of 2,4-dihaloquinazolines is disclosed beginning with methoxycarbonyl- or phenoxycarbonyl-derivatives of substituted phenylureas which are cyclized and concomitantly halogenated with a cyclizing-halogenating reagent such as N,N-dimethylaniline in phosphorus oxychloride. The 2,4-dihaloquinazolines of the instant process are particularly valuable as intermediates in the preparation of 4-amino-2-(4-substituted-piperazin-1-yl) quinazolines useful in the treatment of cardiovascular disorders such as hypertension.

10 Claims, No Drawings

PROCESS FOR PREPARING 2,4-DIHALOQUINAZOLINES

FIELD OF THE INVENTION

This invention is concerned with a new process for the production of 2,4-dihaloquinazolines. These chemical compounds are utilized as intermediates in the preparation of antihypertensive agents such as the various 4-amino-2-(4-substituted piperazin-1-yl)-quinazolines described in Hess, U.S. Pat. Nos. 3,511,836, and 3,669,968 and Partyka, et al., 4,001,237 and 4,001,238.

DESCRIPTION OF THE PRIOR ART

F. H. S. Curd, et al., J. Chem. Soc., 1759 (1948) describes a two-step procedure illustrated by the reaction sequence below for preparation of 2,4-dichloroquinazolines involving first cyclization of an ortho-ureido derivative of various aromatic acids, amides, nitriles and esters with aqueous base or acid to form an intermediate 2,4-(1H,3H)quinazolindione which is then chlorinated with a mixture of phosphorus pentachloride and phosphorus oxychloride or with a mixture of phosphorus oxychloride and N,N-dimethylaniline.

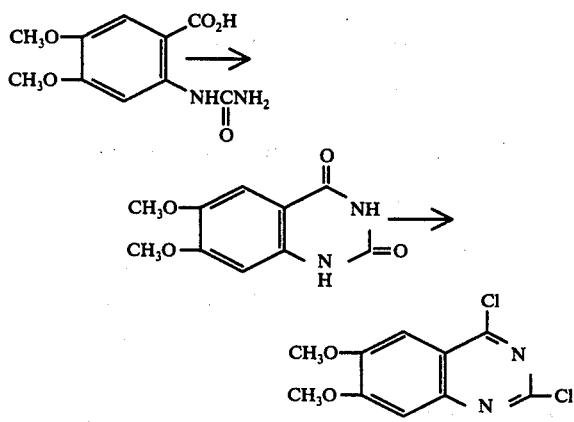

The foregoing procedure of F. H. S. Curd, et al., J. Chem. Soc., 1759 (1948) has been employed in the preparation of various 2,4-dichloroquinazoline intermediates disclosed in Hess, U.S. Pat. Nos. 3,511,836 and Cronin, 3,517,005.

Hess, U.S. Pat. No. 3,769,286 extended the Curd, et al. procedure, supra., to trialkoxyquinazolines by reacting 2-amino-3,4,5-trialkoxybenzoic acids with either sodium or potassium cyanate in an aqueous acidic medium and then cyclizing the ureido intermediate to provide a .6,7,8-trialkoxy-2,4-(1H,3H)quinazolindione ring compound which is subsequently halogenated by treating with either phosphorus oxychloride or phosphorus oxybromide.

Findeisen, U.S. Pat. No. 3,843,652 and K. Findeisen, K. Wagner and H. Holtzchmidt, Synthesis, 599 (1972) describe the preparation of variously substituted 2,4-dichloroquinazolines by the following route:

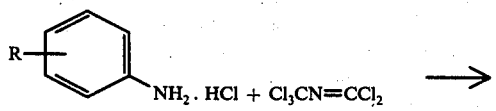

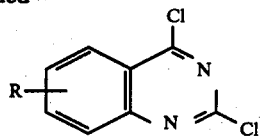

Z. Budesinsky and P. Lederer, Coll. Czech. Chem. Commun., 37, 2779 (1972) report that treatment of 1-aryl-3-acyl ureas with polyphosphoric acid yields 4-aryl (or alkyl) -2(1H)-quinazolinones.

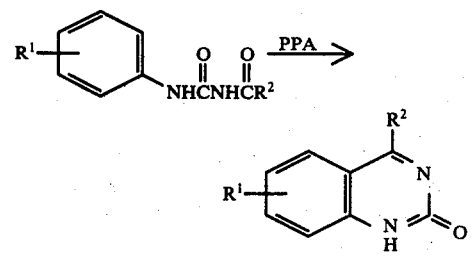

German Pat. No. 2,261,739 (1974) (see Chem. Abs. 81, 84394q (1974)) discloses the following synthesis of quinazolin-2,4-diones:

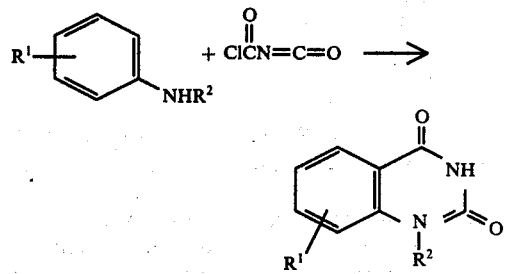

SUMMARY OF THE INVENTION

Broadly described, this invention is concerned with a new process for the preparation of 2,4-dihaloquinazolines of formula I

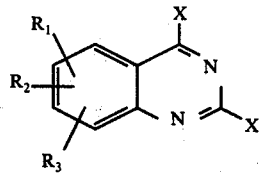

wherein $R_1$, $R_2$ and $R_3$ are independently selected from the group consisting of hydrogen, lower alkyl and lower alkoxy radicals and X is halogen atom selected from the group consisting of chlorine and bromine which involves a one-step conversion of methoxycarbonyl- and phenoxycarbonyl-derivatives of substituted phenylureas to formula I quinazoline products. The single-step process is carried out by treating the urea starting materials with a cyclizing-halogenating reagent selected from the group consisting of hydrogen chloride in phosphorus oxychloride, hydrogen bromide in phosphorus oxybromide, phosphorus oxychloride and N,N-dimethylaniline, and phosphorus oxybromide and N,N-dimethylaniline.

DETAILED DESCRIPTION OF THE INVENTION

As indicated hereinabove, the instant invention is concerned with a process for preparing a compound of formula I

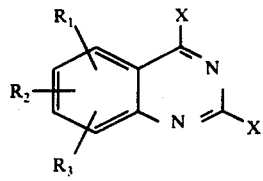

wherein
X is halogen selected from the group consisting of chlorine and bromine; and
R$_1$, R$_2$ and R$_3$ are independently selected from the group consisting of hydrogen, lower alkyl of 1 to 4 carbon atoms inclusive and lower alkoxy of 1 to 4 carbon atoms inclusive;
which comprises treating a compound of formula II

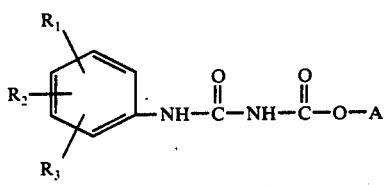

wherein R$_1$, R$_2$ and R$_3$ are as above and A is methyl or phenyl with a cyclizing-halogenating reagent selected from the group consisting of (a) hydrogen chloride in phosphorus oxychloride, (b) hydrogen bromide in phosphorus oxybromide, (c) phosphorus oxychloride and N,N-dimethylaniline, and (d) phosphorus oxybromide and N,N-dimethylaniline until cyclization and halogenation is essentially complete to produce the quinazoline compound of formula I.

Preferred embodiments of the foregoing process for the preparation of compounds characterized by formula I are those wherein:
the compound of formula II employed is 1-(3,4-dimethoxyphenyl)-3-phenoxycarbonylurea;
the compound of formula II employed is 1-(2,3,4-trimethoxyphenyl)-3-phenoxycarbonylurea;
the cyclizing-halogenating reagent is phosphorus oxychloride and N,N-dimethylaniline;
the cyclizing-halogenating reagent is phosphorus oxybromide and N,N-dimethylaniline;
the compound of formula II is treated with N,N-dimethylaniline in a solvent amount of phosphorus oxychloride;
the compound of formula II is treated with N,N-dimethylaniline in a solvent amount of phosphorus oxybromide;
the reaction is carried out at reflux temperature of phosphorus oxychloride or phosphorus oxybromide;
the reaction is carried out at reflux temperature of phosphorus oxychloride or phosphorus oxybromide for a period of 2 to 6 hours.

Another preferred embodiment of the present invention is a process for the preparation of a quinazoline of formula III

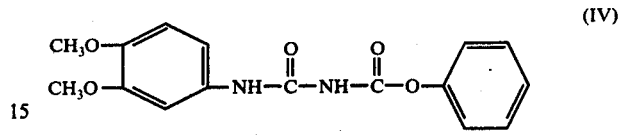

which comprises treating a phenoxycarbonylurea having formula IV

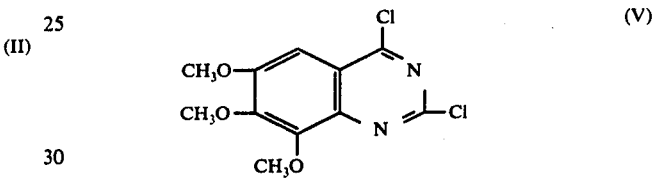

with N,N-dimethylaniline in a solvent amount of phosphorus oxychloride until cyclization and chlorination is essentially complete.

Still another preferred embodiment of the present invention is a process for the preparation of a quinazoline of formula V

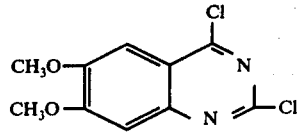

which comprises treating a phenoxycarbonylurea having formula VI

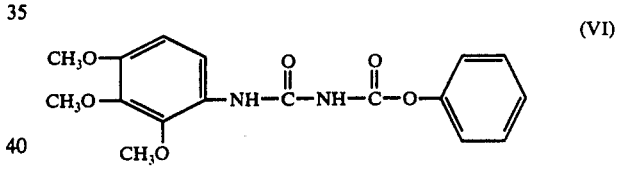

with N,N-dimethylaniline in a solvent amount of phosphorus oxychloride until cyclization and chlorination is essentially complete.

The methoxycarbonylureas and phenoxycarbonylureas of formula II employed as starting materials in the instant process are obtained by reacting aniline or (alkyl or alkoxy) substituted anilines with methoxycarbonylisocyanate or phenoxycarbonylisocyanate, the latter two reagents being prepared according to the procedure of A. J. Speziale, et al., as described in the J. of Organic Chemistry, 30, 4306 (1965).

According to the general process of the instant invention, the phenoxycarbonylureas and 3-methoxycarbonylureas of formula II are intramolecularly cyclized and halogenated in a one-step reaction to provide 2,4-dihaloquinazolines of formula I. This conversion is carried out by treating the 3-methoxycarbonylureas or 3-phenoxycarbonylureas of formula II with a cyclizing-halogenating agent selected from the group consisting of hydrogen chloride in phosphorus oxychloride, hydrogen bromide in phosphorus oxybromide, phosphorus oxychloride and N,N-dimethylaniline, and phosphorus oxybromide and N,N-dimethylaniline. When hydrogen chloride is phosphorus oxychloride or N,N-dimethylaniline and phosphorus oxychloride are employed, 2,4-dichloroquinazolines are obtained. Similarly, when hydrogen bromide in phosphorus oxybromide or N,N-dimethylaniline and phosphorus oxybromide are employed, the products of formula I are the corresponding 2,4-dibromoquinazolines. Generally, the reaction is carried out with the aid of heat, employing solvent amounts of phosphorus oxychloride or phosphorus oxybromide. Yields of the products of formula I wherein X is halogen are optimized with N,N-dimethylaniline in phosphorus oxybromide or phosphorus oxychloride and, accordingly, these cyclization-halogenating reagents are particularly preferred in carrying out the instant process.

Regarding the use herein of the term "solvent amount", it is to be understood that said term refers to a quantity of phosphorus oxychloride or phosphorus oxybromide sufficient to provide good mixing and handling characteristics with respect to the reaction mixture. For this purpose, a ratio of from about 2 to 15 ml. of phosphorus oxychloride or phosphorus oxybromide for each gram of the starting compounds of formula II is generally preferred.

It is also to be understood that by the terms "lower alkyl" and "lower alkoxy", as used herein, it is meant that the carbon chain which comprises these groups include both straight and branched carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

By the term "independently selected", as used herein, it is meant that the $R_1$, $R_2$ and $R_3$ substituents may or may not be identical.

It is also noted that while the working examples are limited to methoxycarbonyl and phenoxycarbonyl for illustrative purposes, extension to other alkoxy and aryloxy (e.g. p-nitrophenoxy)carbonyl derivatives would be obvious to one skilled in the art.

The following examples further illustrate the present invention and will enable others skilled in the art to understand it more completely. It is to be understood that the invention is not limited solely to the particular examples given below. All temperatures expressed herein are in degrees centigrade.

EXAMPLE 1

1-(3,4-Dimethoxyphenyl0-3-phenoxycarbonylurea

To a solution of phenoxycarbonylisocyanate (7.0 g., 0.043 mole) in 50 ml. of dioxane is added 4-aminoveratrole (6.57 g., 0.043 mole) under a nitrogen atmosphere while maintaining a temperature of 20°-25°. Following the addition of the 4-aminoveratrole, a second 50 ml. portion of dioxane is added and the solution refluxed for a period of one hour. Concentration of the reaction mixture under reduced pressure provides an oily solid residue. Titration of this residual material with about 40 ml. of cold carbon tetrachloride followed by crystallization from acetonitrile provides analytically pure 1-(3,4-dimethoxyphenyl)-3-phenoxycarbonylurea, m.p. 139.5°-142°.

Anal. Calcd. for $C_{16}H_{16}N_2O_5$ (%): C, 60.76; H, 5.10; N, 8.86. Found (%): C, 60.34; H, 5.15; N, 9.27.

EXAMPLE 2

1-(3,4-Dimethoxyphenyl)-3-methoxycarbonylurea

To a solution of methoxycarbonylisocyanate (3.78 g. 0.0374 mole) in 45 ml. of dioxane is added 4-aminoveratrole (5.73 g., 0.037 mole) while maintaining a temperature of 20°-30°. After completing the addition, another 45 ml. portion of dioxane is added and the mixture then heated at reflux for a period of one hour. Evaporation of the solvent and crystallization of residual material from nitromethane provides analytically pure 1-(3,4-dimethoxyphenyl)-3-methoxycarbonylurea, m.p. 168°-170°.

Anal. Calcd. for $C_{11}H_{14}N_2O_5$ (%): C, 51.97; H, 5.55; N, 11.02. Found (%): C, 52.11; H, 5.40; N, 10.81.

EXAMPLE 3

2,4-Dichloro-6,7-dimethoxyquinazoline (a) One ml. of N,N-dimethylaniline is added to 10 ml. of phosphorus oxychloride at 20°-25°. After a period of 5 min. 1-(3,4-dimethoxyphenyl)-3-phenoxycarbonylurea (0.785 g., 2.4 mmole) is added and the solution heated to reflux for a period of 4 hours. After the reflux period, excess phosphorus oxychloride is removed under reduced pressure providing a dark oily residue which is dissolved in chloroform. The chloroform solution is added cautiously to an ice/water mixture and after 10 min. the organic layer is separated and the aqueous phase extracted with additional chloroform. Combined chloroform extracts are sequentially washed with water, aqueous 1.0 N hydrochloric acid, water, aqueous 0.5 N sodium hydroxide and finally water. After drying the solution over sodium sulfate, the chloroform extract is concentrated under reduced pressure to provide 0.92 g. of a yellow-brown solid. Chromatographic purification of this material employing an aluminum oxide column eluted with toluene affords 0.504 g. of yellow solid. Trituration of this material with cold ethanol affords 0.368 g. (58% yield) of 2,4-dichloro-6,7-dimethoxyquinazoline, m.p. 175°-177°; mixture melting point (174°-177°; with sample: m.p. 158.5°-162°, prepared according to Curd, et al., J. Chem. Soc., 1765, (1948) and otherwise identical according to infrared, nuclear magnetic resonance and vaporphase chromatograph analysis.

(b) When the above procedure is repeated employing equimolar amount 1-(3,4-dimethoxyphenyl)-3-methoxycarbonylurea in place of 1-(3,4-dimethoxyphenyl)-3-phenoxycarbonylurea, the title compound 2,4-dichloro-6,7-dimethoxyquinazoline is produced.

(c) Hydrogen chloride gas is bubbled into a suspension of 1-(3,4-dimethoxyphenyl)-3-methoxycarbonylurea (0.5 g.) in 17 ml. of phosphorus oxychloride for about 3 min. and the mixture then refluxed for a period of 5 hrs. Excess phosphorus oxychloride is evaporated under reduced pressure and residual material dissolved in chloroform which is washed with water, dried and evaporated to provide the 2,4-dichloro-6,7-dimethoxyquinazoline product.

EXAMPLE 4

Following the procedure of Example 1 but employing an equimolar amount of anilines listed below:
aniline,
2-methylaniline,
3-methylaniline,
4-methylaniline,
3-n-butylaniline,
4-isopropylaniline,
2,4-dimethylaniline,
3,4-dimethylaniline,
2,3,4-trimethylaniline,
2-methoxyaniline,
3-methoxyaniline,
4-methoxyaniline, 3-n-butoxyaniline,
4-isopropoxyaniline,
2,4-dimethoxyaniline,
2,3,4-trimethoxyaniline,
in place of 4-aminoveratrole, there is produced, respectively:
(a) 1-phenyl-3-phenoxycarbonylurea,
(b) 1-(2-methylphenyl)-3-phenoxycarbonylurea,
(c) 1-(3-methylphenyl)-3-phenoxycarbonylurea,
(d) 1-(4-methylphenyl)-3-phenoxycarbonylurea,
(e) 1-(3-n-butylphenyl)-3-phenoxycarbonylurea,
(f) 1-(4-isopropylphenyl)-3-phenoxycarbonylurea,
(g) 1-(2,4-dimethylphenyl)-3-phenoxycarbonylurea,
(h) 1-(3,4-dimethylphenyl)-3-phenoxycarbonylurea,
(i) 1-(2,3,4-trimethylphenyl)-3-phenoxycarbonylurea,
(j) 1-(2-methoxyphenyl)-3-phenoxycarbonylurea,
(k) 1-(3-methoxyphenyl)-3-phenoxycarbonylurea,
(l) 1-(4-methoxyphenyl)-3-phenoxycarbonylurea,
(m) 1-(3-n-butoxyphenyl)-3-phenoxycarbonylurea,
(n) 1-(4-isopropoxyphenyl)-3-phenoxycarbonylurea,
(o) 1-(2,4-dimethoxyphenyl)-3-phenoxycarbonylurea,
(p) 1-(2,3,4-trimethoxyphenyl)-3-phenoxycarbonylurea.

EXAMPLE 5

Following the procedure of Example 3(A) but employing an equimolar amount of phenoxycarbonylureas listed below:
1-phenyl-3-phenoxycarbonylrea,
1-(2-methylphenyl)-3-phenoxycarbonylurea,
1-(3-methylphenyl)-3-phenoxycarbonylurea,
1-(4-methylphenyl)-3-phenoxycarbonylurea,
1-(3-n-butylphenyl)-3-phenoxycarbonylurea,
1-(4-isopropylphenyl)-3-phenoxycarbonylurea,
1-(2,4-dimethylphenyl)-3-phenoxycarbonylurea,
1-(3,4-dimethylphenyl)-3-phenoxycarbonylurea,
1-(2,3,4-trimethylphenyl)-3-phenoxycarbonylurea,
1-(2-methoxyphenyl)-3-phenoxycarbonylurea,
1-(3-methoxyphenyl)-3-phenoxycarbonylurea,
1-(4-methoxyphenyl)-3-phenoxycarbonylurea,
1-(3-n-butoxyphenyl)-3-phenoxycarbonylurea,
1-(4-isopropoxyphenyl)-3-phenoxycarbonylurea,
1-(2,4-dimethoxyphenyl)-3-phenoxycarbonylurea,
1-(2,3,4-trimethoxyphenyl)-3-phenoxycarbonylurea,
in place of 1-(3,4-dimethoxyphenyl)-3-phenoxycarbonylurea, there is produced, respectively:
(a) 2,4-dichloro-quinazoline,
(b) 2,4-dichloro-8-methylquinazoline,
(c) 2,4-dichloro-7-methylquinazoline,
(d) 2,4-dichloro-6-methylquinazoline,
(e) 2,4-dichloro-7-n-butylquinazoline,
(f) 2,4-dichloro-6-isopropylquinazoline,
(g) 2,4-dichloro-6,8-dimethylquinazoline,
(h) 2,4-dichloro-6,7-dimethylquinazoline,
(i) 2,4-dichloro-6,7,8-trimethylquinazoline,
(j) 2,4-dichloro-8- methoxyquinazoline,
(k) 2,4-dichloro-7-methoxyquinazoline,
(l) 2,4-dichloro-6-methoxyquinazoline,
(m) 2,4-dichloro-7-n-butoxyquinazoline,
(n) 2,4-dichloro-6-isopropoxyquinazoline,
(o) 2,4-dichloro-6,8-dimethoxyquinazoline,
(p) 2,4-dichloro-6,7,8-trimethoxyquinazoline.

EXAMPLE 6

2,4-Dibromo-6,7-dimethoxyquinazoline

The title compound is obtained by reacting 1-(3,4-dimethoxyphenyl)-3-phenoxycarbonylurea with phosphorus oxybromide and N,N-dimethylaniline according to the procedure of Example 3(a).

What is claimed is:

1. A process for preparing a compound of formula I

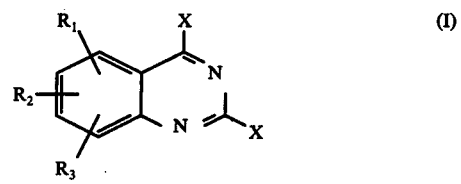

wherein
X is halogen selected from the group consisting of chlorine and bromine; and
$R_1$, $R_2$ and $R_3$ are independently selected from the group consisting of hydrogen, lower alkyl of 1 to 4 carbon atoms inclusive and lower alkoxy of 1 to 4 carbon atoms inclusive;
which comprises treating a compound of formula II

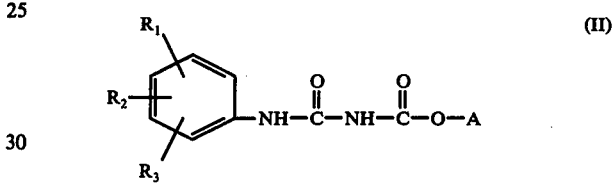

wherein $R_1$, $R_2$ and $R_3$ are as above and A is methyl or phenyl with a reagent selected from the group consisting of (a) hydrogen chloride in phosphorus oxychloride, (b) hydrogen bromide in phosphorus oxybromide, (c) phosphorus oxychloride and N,N-dimethylaniline, and (d) phosphorus oxybromide and N,N-dimethylaniline and thereafter completing the cyclization and halogenation reaction by heating at reflux temperature to produce the quinazoline compound of formula I.

2. The process of claim 1 wherein the compound of formula II employed is 1-(3,4-dimethoxyphenyl)-3-phenoxycarbonylurea.

3. The process of claim 1 wherein the compound of formula II employed is 1-(2,3,4-trimethoxyphenyl)-3-phenoxycarbonylurea.

4. The process of claim 1 wherein the cyclizing-halogenating reagent is phosphorus oxychloride and N,N-dimethylaniline.

5. The process of claim 1 wherein the cyclizing-halogenating reagent is phosphorus oxybromide and N,N-dimethylaniline.

6. The process of claim 1 wherein the compound of formula II is treated with N,N-dimethylaniline in a solvent amount of phosphorus oxychloride.

7. The process of claim 1 wherein the compound of formula II is treated with N,N-dimethylaniline in a solvent amount of phosphorus oxybromide.

8. The process of claim 1 wherein the reaction is carried out in phosphorus oxychloride or phosphorus oxybromide with a reflux period of 2 to 6 hours.

9. A process for the preparation of a quinazoline of formula III

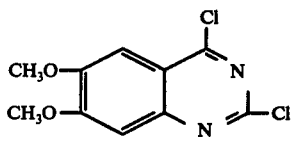 (III)

which comprises treating a phenoxycarbonylurea having formula IV

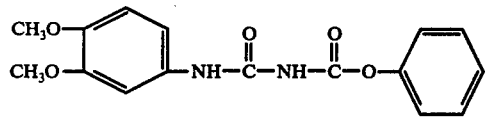 (IV)

with N,N-dimethylaniline in a solvent amount of phosphorus oxychloride and thereafter refluxing the reaction mixture to complete the cyclization and chlorination reaction.

10. A process for the preparation of a quinazoline of formula V

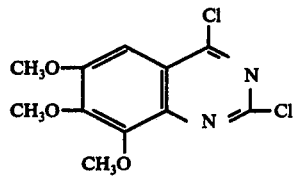 (V)

which comprises treating a phenoxycarbonylurea having formula VI

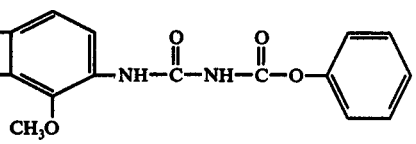 (VI)

with N,N-dimethylaniline in a solvent amount of phosphorus oxychloride and thereafter refluxing the reaction mixture to complete the cyclization and chlorination reaction.

* * * * *